United States Patent [19]

Link

[11] Patent Number: 4,651,747

[45] Date of Patent: Mar. 24, 1987

[54] WAVEFORM INFORMATION OBTAINING TECHNIQUES ASSOCIATED WITH AN INDIVIDUAL'S BLOOD PRESSURE

[75] Inventor: William T. Link, Berkeley, Calif.

[73] Assignee: Baxter Travenol Laboratories, Inc., Deerfield, Ill.

[21] Appl. No.: 868,314

[22] Filed: May 28, 1986

Related U.S. Application Data

[63] Continuation-in-part of Ser. No. 622,073, Jun. 19, 1984.

[51] Int. Cl.$^4$ .................................................. A61B 5/02
[52] U.S. Cl. ...................................... 128/677; 128/672
[58] Field of Search ......................... 128/672, 677–683

[56] References Cited

U.S. PATENT DOCUMENTS

| | | | |
|---|---|---|---|
| 3,903,872 | 9/1975 | Link ....................................... | 128/681 |
| 4,009,709 | 3/1977 | Link et al. ........................... | 128/683 X |
| 4,074,711 | 2/1978 | Link et al. ............................. | 128/681 |
| 4,271,843 | 6/1981 | Flynn ...................................... | 128/681 |
| 4,367,751 | 1/1983 | Link et al. ............................. | 128/682 |

OTHER PUBLICATIONS

Link; "Norse Systems Automatic Electronic Blood Pressure Monitor Using Waveform Analysis Oscillometry"; 11-1974, pp. 1-10.

Primary Examiner—Kyle L. Howell
Assistant Examiner—Angela D. Sykes
Attorney, Agent, or Firm—Flehr, Hohbach, Test, Albritton & Herbert

[57] ABSTRACT

Techniques for determining different parameters associated with an individual's blood pressure in a non-invasive manner are disclosed herein. These techniques include generating a blood pressure waveform corresponding to the individual's actual waveform whereby the mean blood pressure of the individual can be readily calculated. This is accomplished by either using a specifically selected cuff pressure or by ramping the cuff pressure as would be done in taking blood pressure.

20 Claims, 12 Drawing Figures

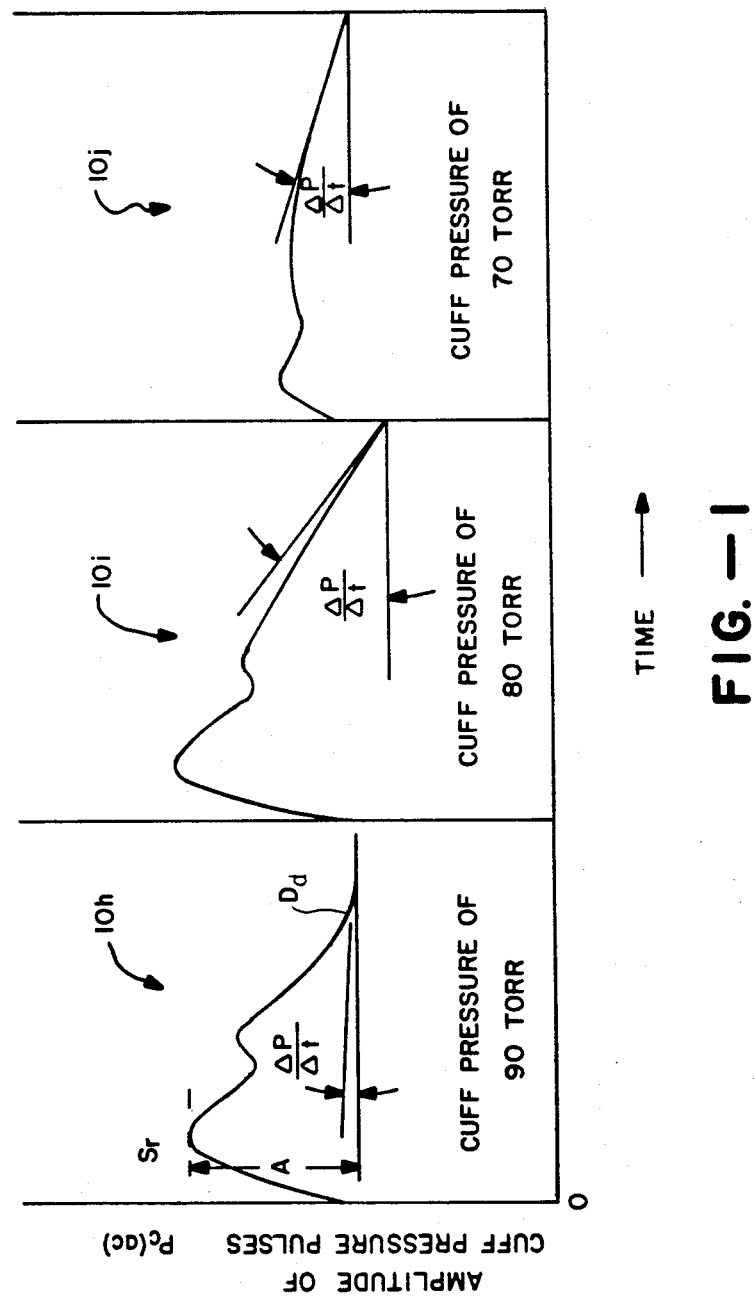

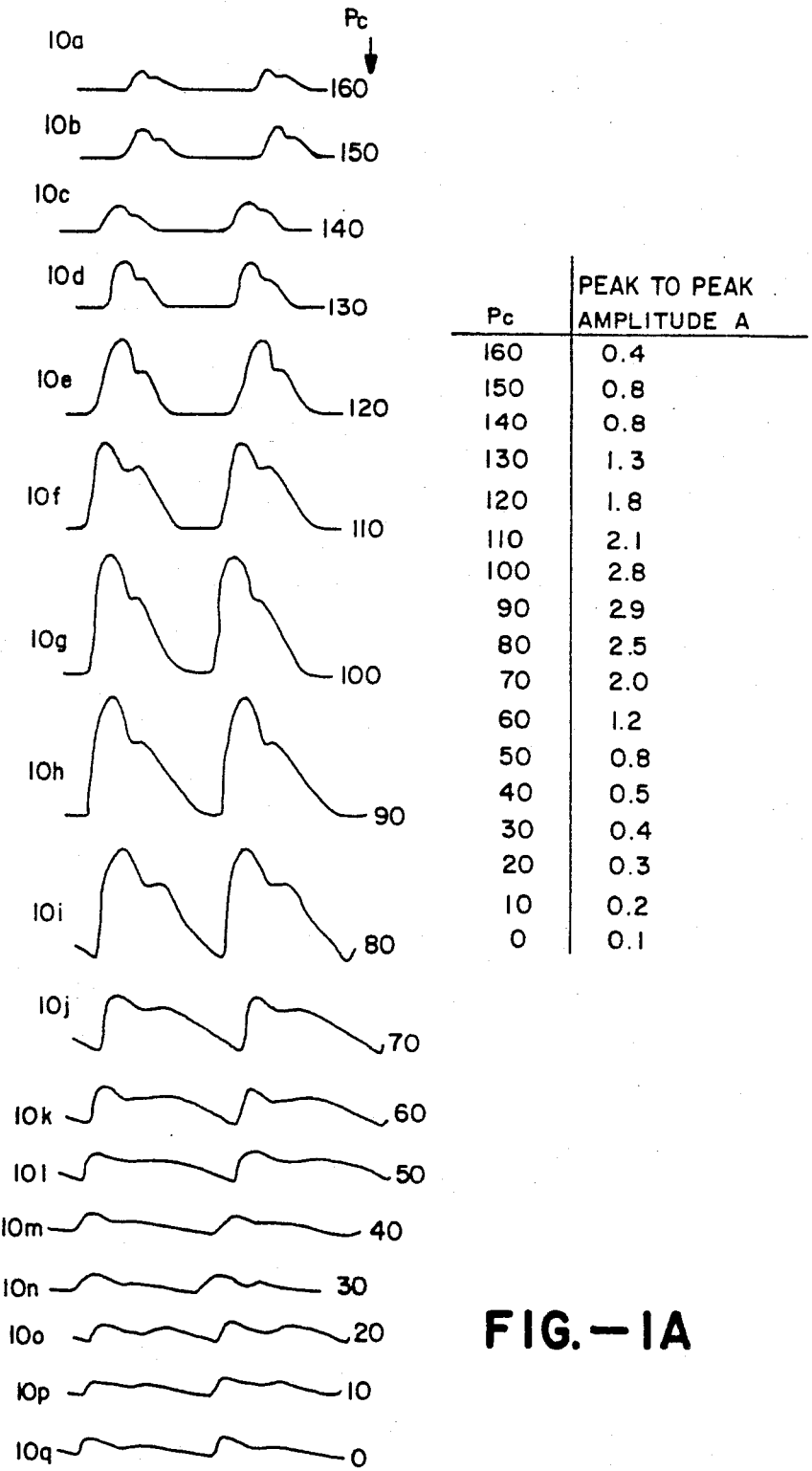
FIG.—1A

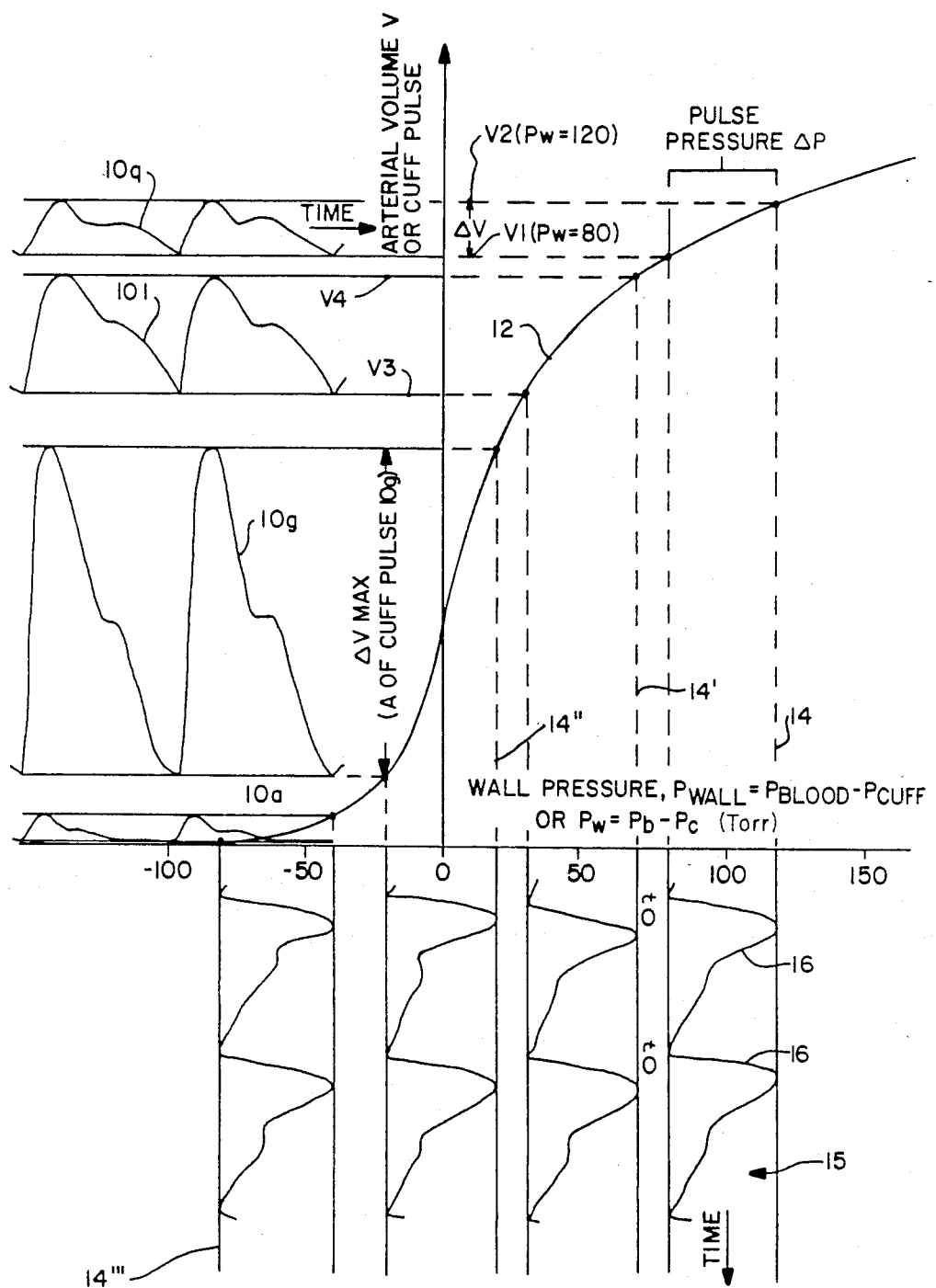
FIG.—2

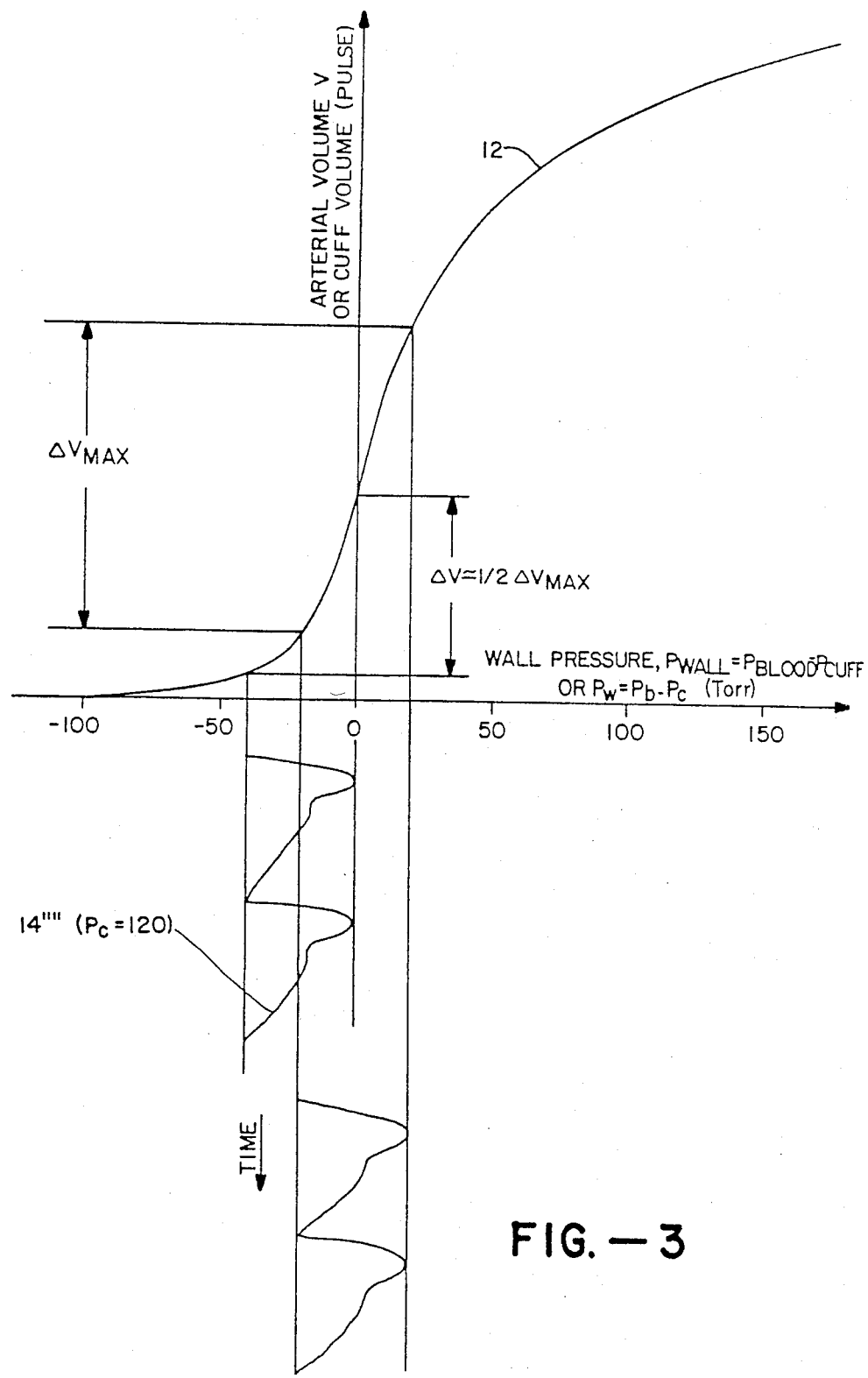
FIG.—3

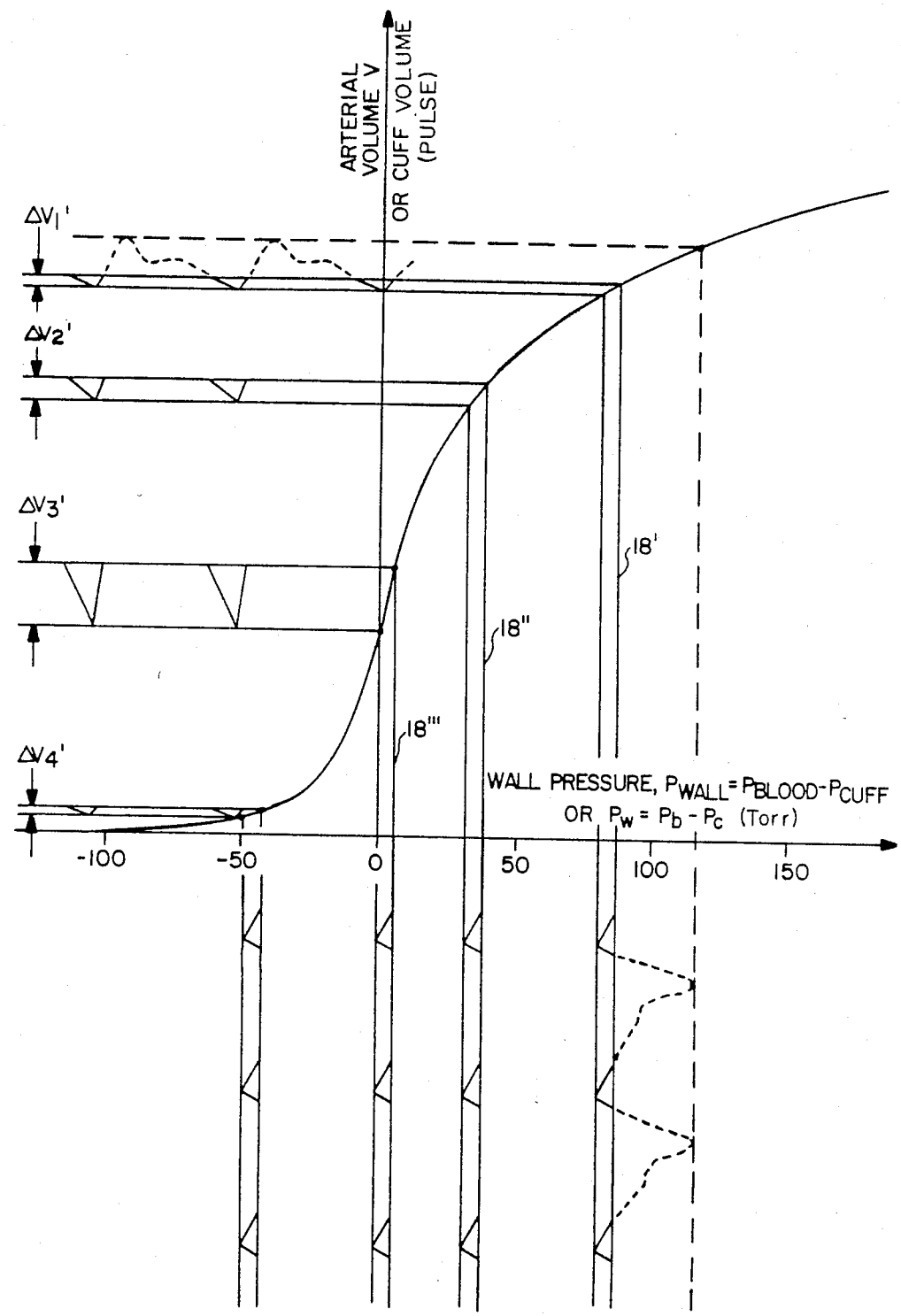
FIG.—4

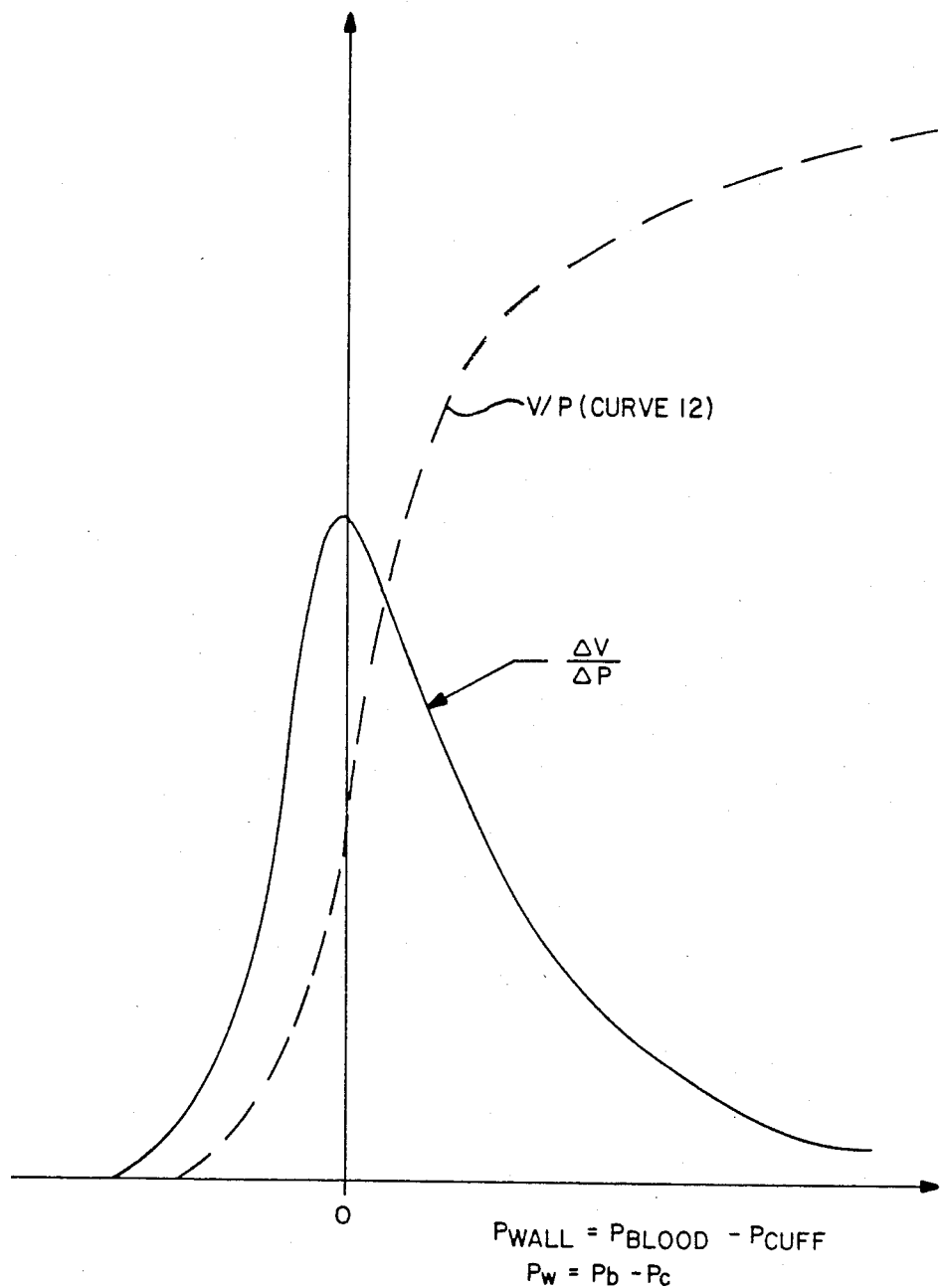
FIG. — 5

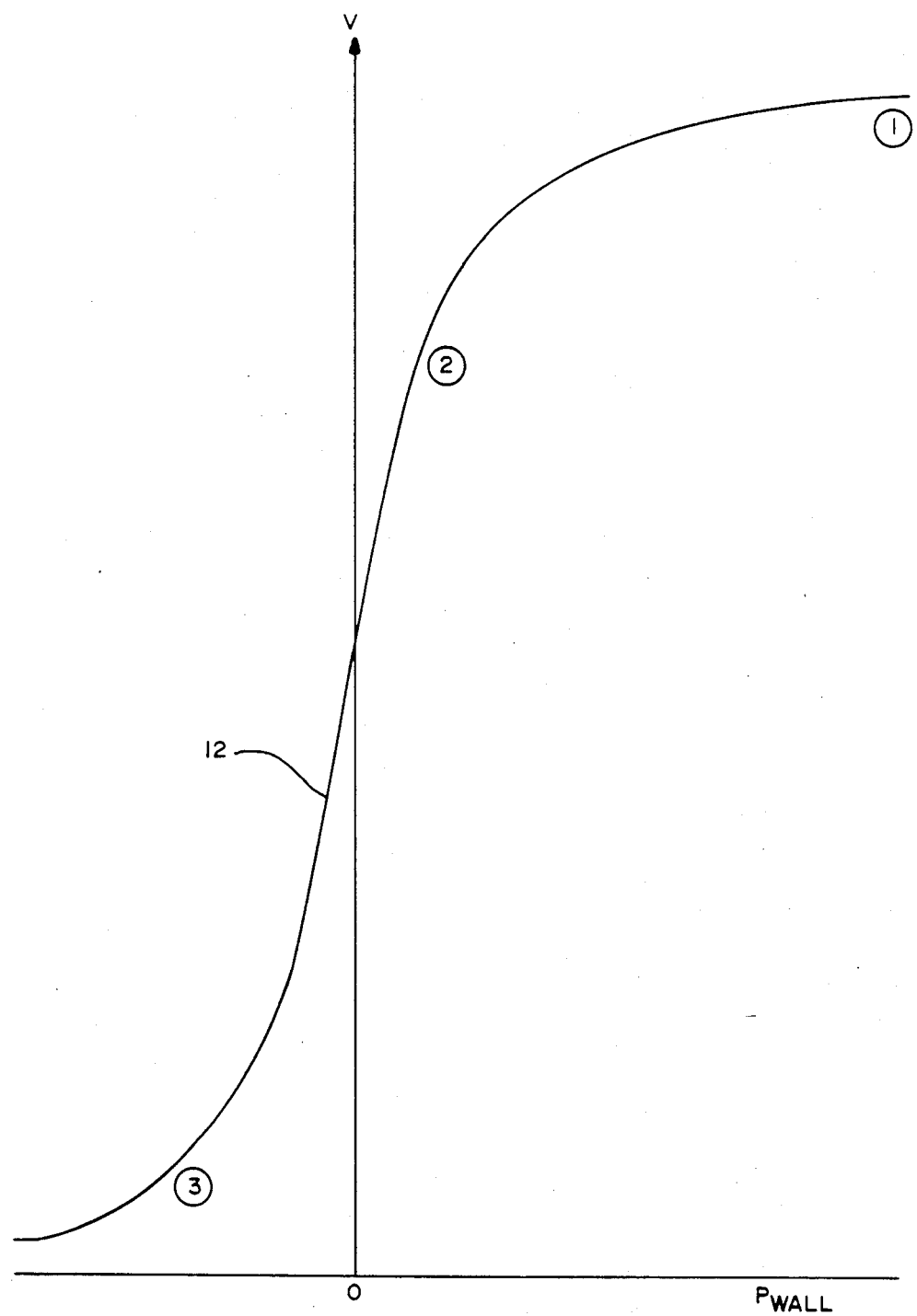
FIG.—6

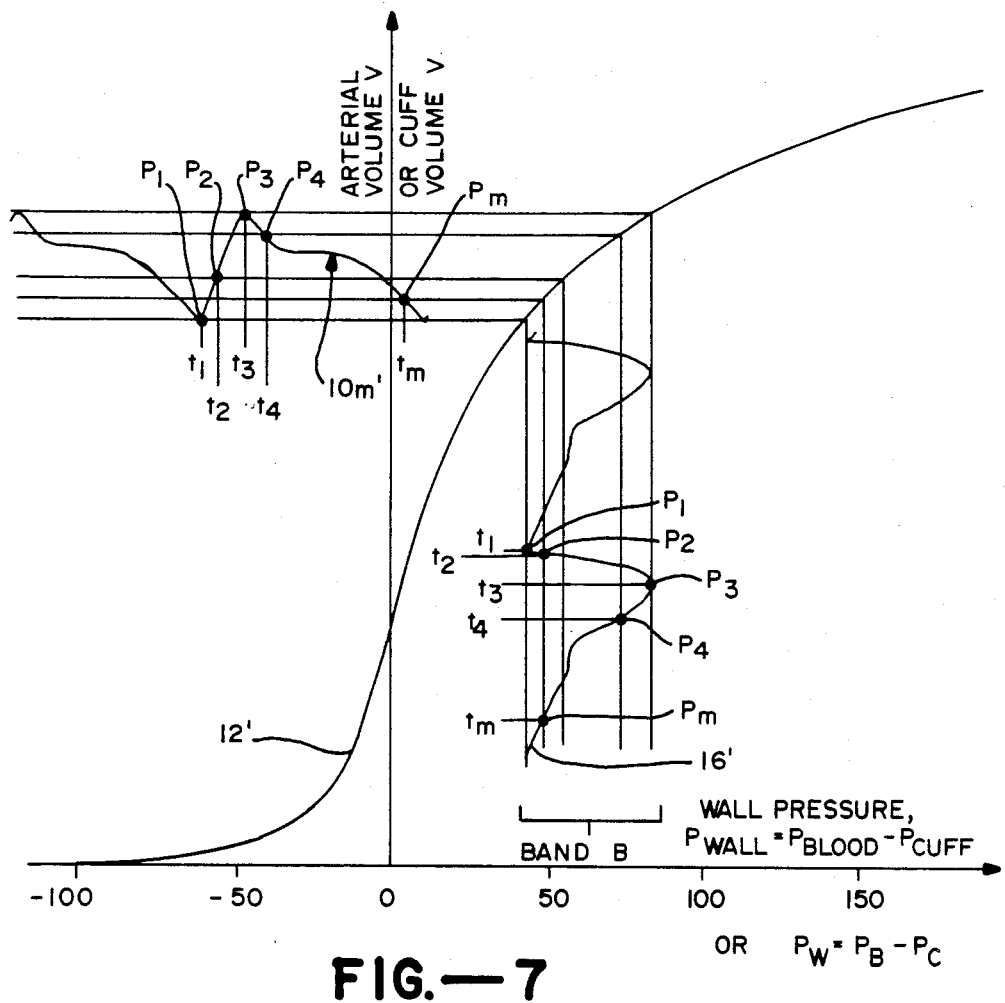
FIG.—7
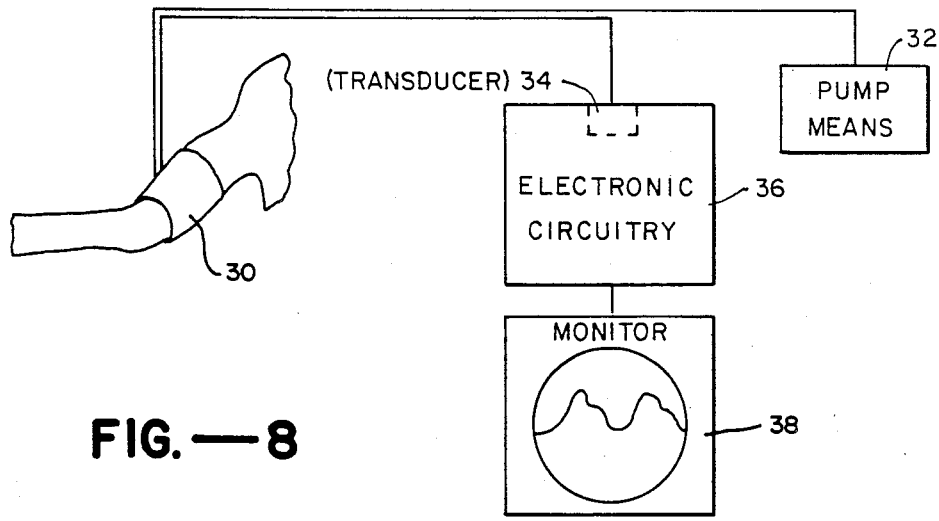
FIG.—8

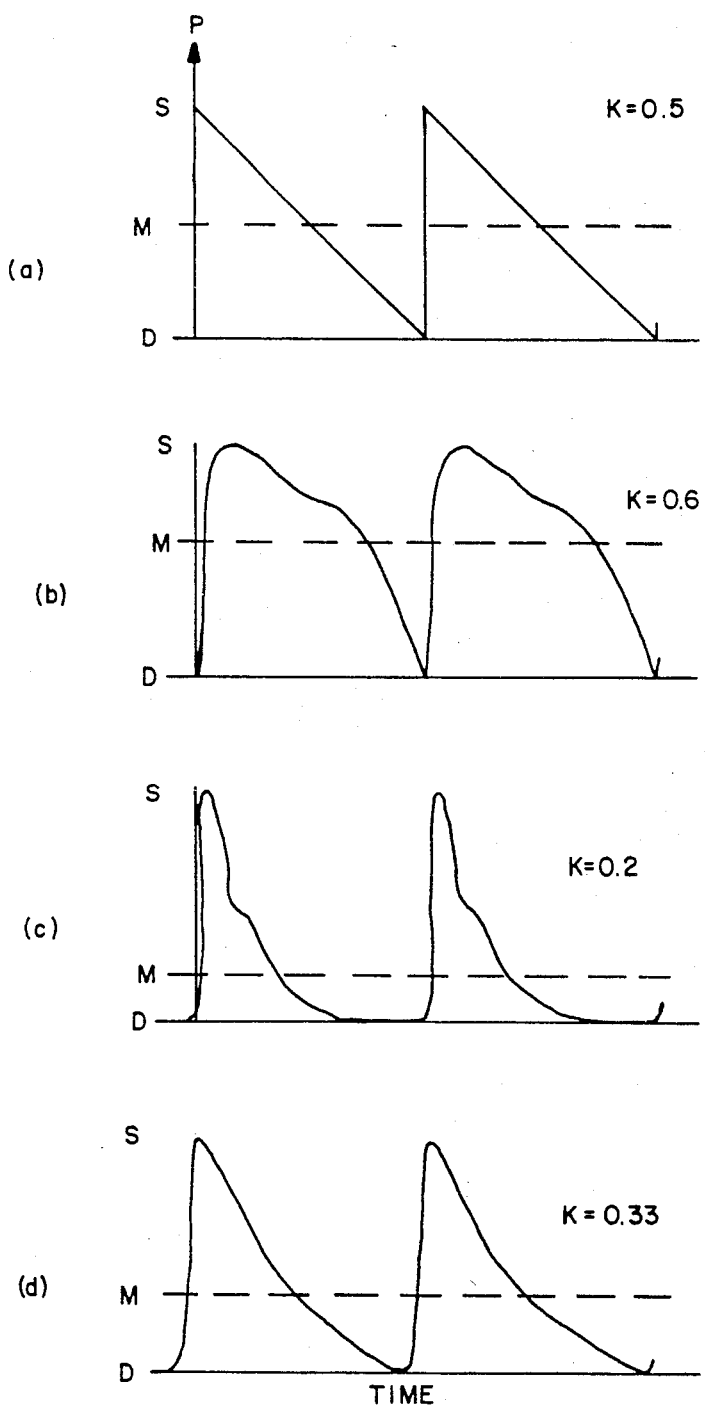
FIG.—9

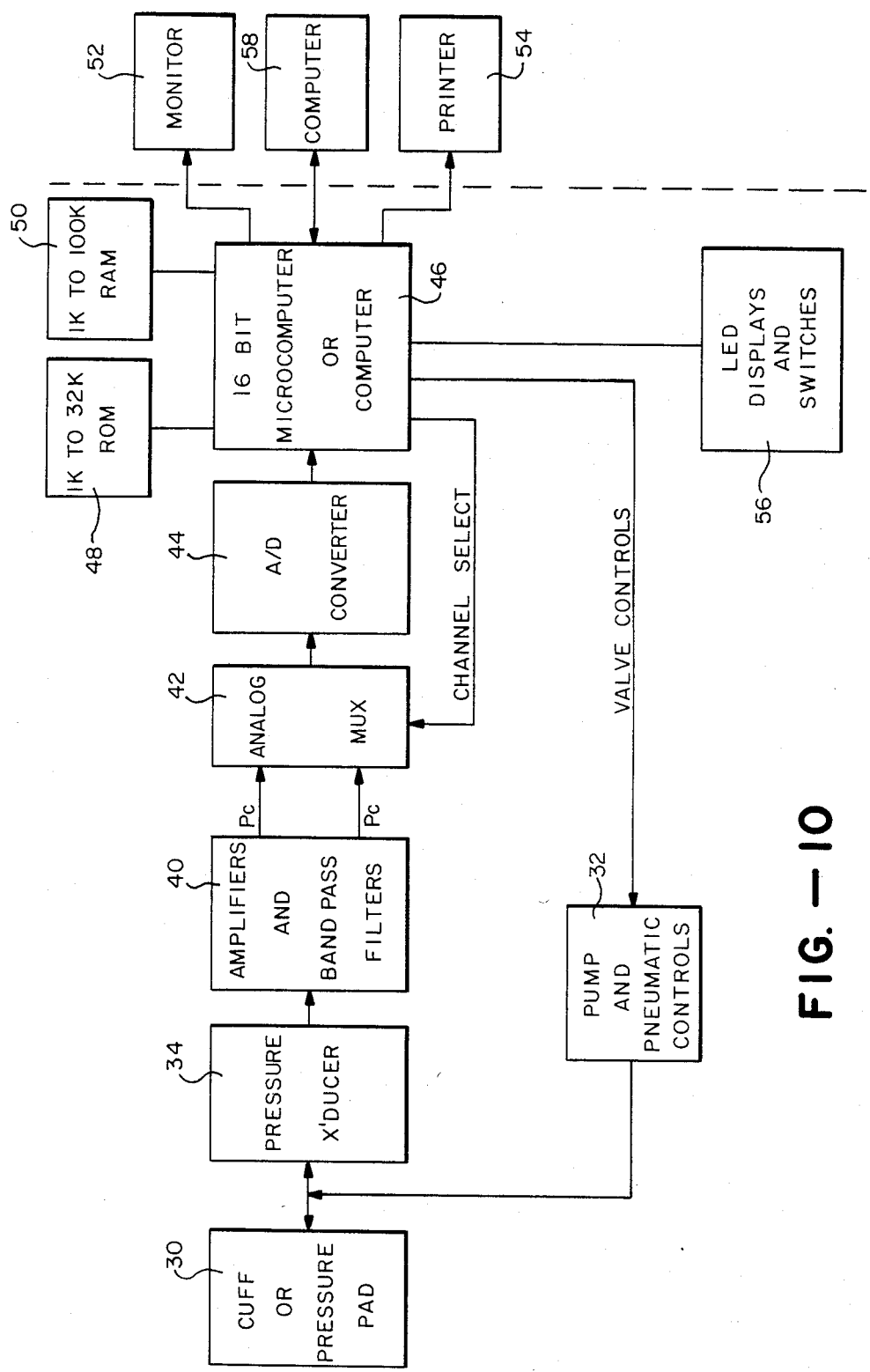
FIG.—10

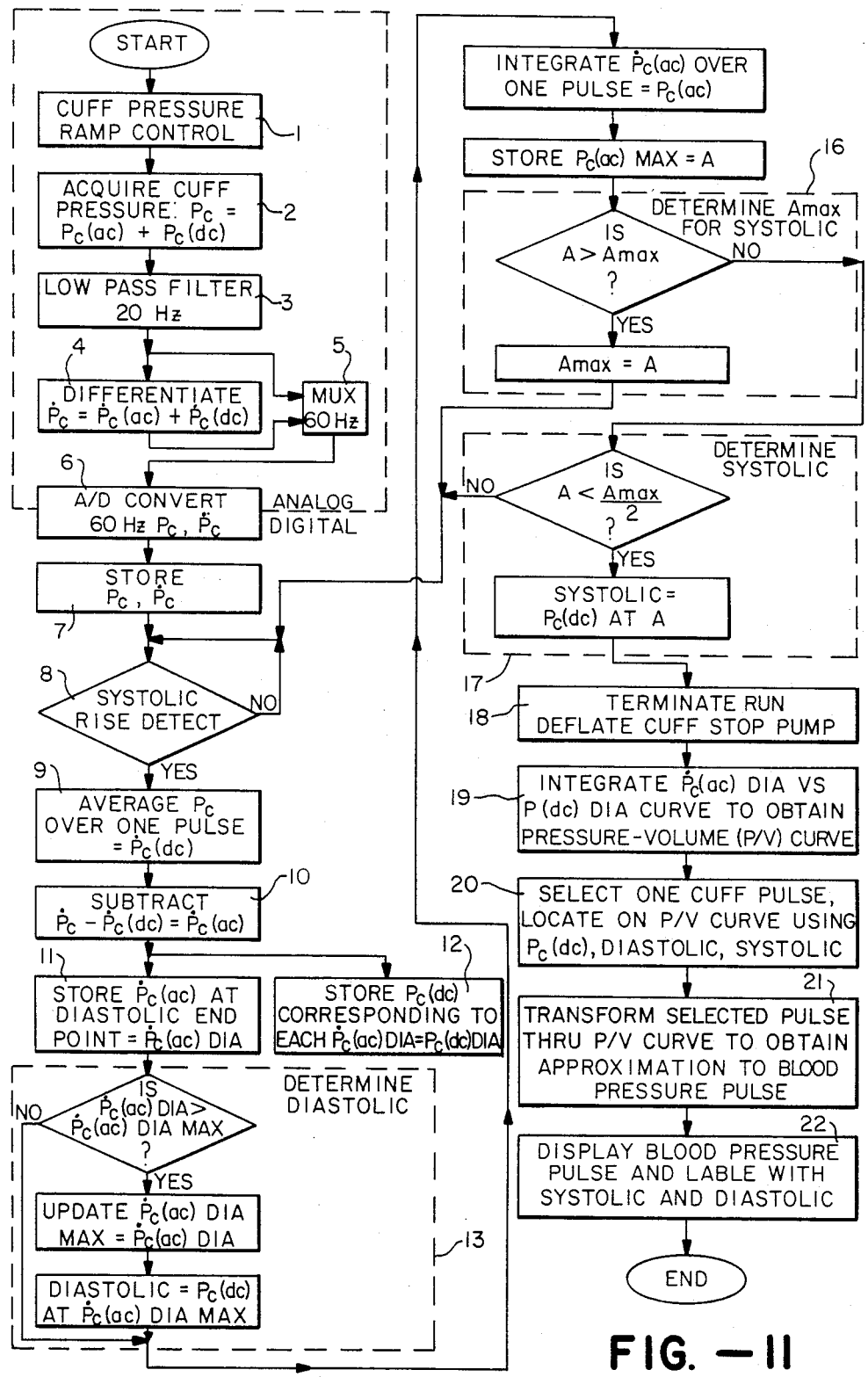
FIG. —11

WAVEFORM INFORMATION OBTAINING TECHNIQUES ASSOCIATED WITH AN INDIVIDUAL'S BLOOD PRESSURE

This is a continuation-in-part of U.S. patent application Ser. No. 622,073 filed June 19, 1984.

BACKGROUND OF THE INVENTION

The present invention relates generally to blood pressure evaluation procedures and more particularly to non-invasive techniques for determining certain waveform information associated with blood pressure.

The most reliable ways presently known for obtaining information relating to an individual's blood pressure require invasive procedures. Such procedures are not carried out routinely but only under extreme circumstances, for example during heart surgery. Under less critical conditions, blood pressure information including specifically an individual's systolic (maximum) and diastolic (minimum) blood pressures is obtained non-invasive. There are two well known non-invasive techniques presently being used today, one is commonly referred to as auscultation and the other is based on oscillometry. Both of these non-invasive techniques use the standard arm cuff which most people are familiar with. However, in the auscultatory method, the systolic and diastolic pressures are determined by listening to certain sounds (Korotkoff sounds) which occur as a result of the cuff first being pressurized and then depressurized whereas oscillometry actually measures changes in pressure in the cuff as a result of changes in blood pressure as the cuff is first pressurized and then depressurized.

As will be seen hereinafter, the various embodiments of the present invention are based on oscillometry. In order to more fully appreciate these embodiments, reference is made to applicant's own U.S. Pat. No. 3,903,872 (the Link patent) for obtaining blood pressure information non-invasively. This patent which is incorporated herein by reference describes, among other things, a way of obtaining the diastolic pressure of an individual in accordance with a technique which will be discussed in more detail hereinafter. In U.S. Pat. Nos. 4,009,709 and 4,074,711 (Link et al) which are also incorporated herein by reference, non-invasive techniques using oscillometry are disclosed for obtaining the systolic pressure of an individual. These techniques will also be discussed hereinafter.

OBJECTS AND SUMMARY OF THE INVENTION

While the various procedures described in the Link and Link et al patents just recited and other patents held by applicant are satisfactory for their intended purposes, it is an object of the present invention to provide additional uncomplicated and yet reliable techniques for obtaining different types of information relating to an individual's blood pressure.

A more specific object of the present invention is to provide a different uncomplicated and yet reliable technique for generating non-invasively a waveform closely approximating an individual's true blood pressure waveform which, heretofore, has been obtainable by invasive means only.

Another particular object of the present invention is to provide a new way for measuring and calculating the mean arterial pressure of an individual.

As will be described in more detail hereinafter, the objects just recited are achieved by means of oscillometry. In accordance with this technique, a suitably sized cuff, for example one which is 20 inches long and 5 inches wide, is positioned around the upper arm of an individual, a human being specifically or a mammal in general (hereinfter referred to as the patient) and initially pressurized to a level which is believed to be clearly greater than the patient's systolic pressure, for example 180 Torr. It is assumed that this pressure will also cause the patient's artery within the sleeve to completely collapse. Thereafter, cuff pressure is gradually reduced toward zero during which time the cuff continuously changes in pressure in an oscillating fasion due to the combination of (1) the internal blood pressure changes in the patient's artery and (2) changes in cuff pressure. The latter at any given time in the procedure is known and oscillatory changes in cuff pressure can be readily measured, for example with an oscilloscope. By using these two parameters in conjunction with information which may be made available from methods disclosed in the above-recited U.S. patents it is possible to achieve the foregoing objectives in an uncomplicated and reliable way utilizing the techniques of the present invention to be described hereinafter.

In this regard, it should be noted at the outset that the typically 5" wide pressure cuff entirely surrounds a corresponding 5" length of artery. The tissue of the arm is for the most part incompressible, and therefore any change in the volume of the artery, caused for example by pulsations of blood, results in a corresponding change in the volume of air in the air bladder which is within the cuff and therefore adjacent to the arm. This change in air volume produces a small but accurately measurable pressure change in the air. This equivalence of pressure pulsations in the cuff bladder to volume pulsations of the artery is the essence of oscillometry.

BRIEF DESCRIPTION OF THE DRAWINGS

In order to more fully appreciate the various techniques of the present invention, the following more detailed background information is provided in conjunction with FIGS. 1-5 of the drawings where:

FIG. 1 (corresponding to FIG. 6 in U.S. Pat. No. 3,903,872) diagrammatically illustrates the shapes of successive cuff pressure versus time pulses (cuff pulses) as the measured cuff pressure changes from 90 Torr to 80 Torr to 70 Torr, assuming the patient has a diastolic pressure of 80 Torr;

FIG. 1A diagrammatically illustrates a full series of cuff pulses corresponding to those in FIG. 1 from a cuff pressure of 160 Torr to a cuff pressure of zero;

FIG. 2 diagrammatically illustrates a curve corresponding to arterial or cuff volume (V), that is, the volume of the patient's artery within the cuff (as measured by cuff volume) versus wall pressure ($P_w$) across the artery wall within the cuff and, superimposed on this curve, a curve which is intended to correspond to the actual blood pressure waveform of a patient, the two curves being provided together in order to illustrate the principles of oscillometry, as relied upon in the above-recited patents;

FIGS. 3 and 4 diagrammatically illustrate the cuff curve of FIG. 1 in ways which display techniques for obtaining a given patient's systolic and diastolic blood pressures in accordance with the Link and Link et al patents recited above; and FIG. 5 diagrammatically illustrates a compliance curve for the patient's artery, that is, a curve which displays the ration $\Delta V/\Delta P$ against the arterial wall pressure $P_w$, where $\Delta V$ is the incremental change in the arterial volume corresponding to a preselected constant change in blood pressure $\Delta P$. This curve is initially determined in order to provide the cuff or arterial volume curve (V/P curve) of FIG. 2 by means of integration, as will be seen;

FIG. 6 diagrammatically illustrates an arterial v/p curve of a given individual with specific emphasis on the degree of linearity of its segments;

FIG. 7 diagrammatically illustrates the use of the arterial curve of FIG. 6 in combination with the given individual's cuff pulses at a fixed cuff pressure to approximate the individual's actual blood pressure curve;

FIG. 8 schematically illustrates an arrangement for providing the approximated curve just referred to in association with FIG. 7;

FIGS. 9 (a)-(d) diagrammatically illustrate four blood pressure waveforms having different blood pressure constants K and equivalently, different mean blood pressures; and FIGS. 10 and 11, respectively, illustrate a block diagram and flow diagram of the technique described with respect to FIGS. 6-8.

FURTHER BACKGROUND OF THE INVENTION

Turning first to FIG. 1, this figure diagrammatically illustrates three successive waveforms $10h$, $10i$ and $10j$ which correspond to the change in volume in a pressurized cuff, as described above, at three different cuff pressures, specifically cuff pressures of 90 Torr, 80 Torr and 70 Torr. In actual practice, a greater number of waveforms (hereinafter referred to as cuff pulses) are generated starting at a cuff pressure of 160 Torr and ending at a cuff pressure of zero, as will be seen in FIG. 1A. By generating these waveforms at known cuff pressures, both the diastolic and systolic pressures of a patient can be determined in accordance with the above-recited patents. While this will be explained in more detail below, it is important to note initially that each waveform has what may be referred to as a systolic rise $S_r$ at one end of the waveform, a diastolic decline $D_d$ at the opposite end and a maximum amplitude A.

While the systolic rise $S_r$ is fairly consistent and distinctive from one cuff pulse 10 to another, both the diastolic decline $D_d$ and amplitude A vary from pulse to pulse for reasons to be explained hereinafter. It is because of these variations that the techniques disclosed in the Link ad Link et al patents recited above are able to determine the diastolic and systolic pressures. Specifically, as will be seen, when the diastolic pressure of a patient is equal to the cuff pressure, the cuff pulse generated has a diastolic decline which is greater in slope than the diastolic decline of any of the other cuff pulses. Thus, assuming that the diastolic decline has a maximum slope at the cuff pulse $10i$ illustrated in FIG. 1, the patient providing these waveforms would have a diastolic pressure of 80 Torr. At the same time, this patient's systolic pressure can be determined by first finding which of the cuff pulses displays a maximum amplitude A and then, moving up in cuff pressure, finding the cuff pulse having half that amplitude. The cuff pressure responsible for producing this half-amplitude pulse will equal the patient's systolic blood pressure. In order to more fully understand these capabilities, reference is made to FIGS. 2-5 in conjunction with the above-recited Link and Link et al patents.

Turning now to FIG. 2, attention is directed to the curves illustrated there in order to explain why the cuff pulses of FIG. 1 result from changes in cuff pressure. The generally S-shaped curve 12 illustrated is shown within a horizontal/vertical coordinate system where the horizontal axis represents the wall pressure $P_w$ across the artery wall of a given patient, within the confines of the applied cuff, and the vertical axis represents arterial volume V of the artery within the cuff, as measured by the internal volume of the cuff itself. In order to fully understand this V/P curve (hereinafter merely referred to as an arterial or a cuff curve), it is important to keep in mind the definition of $P_w$. The wall pressure $P_w$ of the artery of the patient at any given time is equal to the blood pressure $P_b$ of the patient within the artery at that time less the applied pressure of the cuff $P_c$. Thus:

$$P_w = P_b - P_c \quad (1)$$

For purposes of the present discussion, it will be assumed that pressure is measured in Torr (mmHg) and that the section of the horizontal axis to the right of the vertical axis represents positive wall pressures while the section of the axis to the left of the vertical axis represents negative wall pressures. As a result, when no pressure is applied to the cuff (e.g. $P_c=0$), $P_w$ at any given point in time is equal to the blood pressure of the patient at that time. As the cuff is pressurized, $P_w$ decreases (moves to the left along the horizontal axis). When the cuff pressure $P_c$ is equal to the blood pressure $P_b$ at any given point in time, $P_w$ at that time is equal to zero (e.g. at the vertical axis). As the cuff pressure is increased beyond the blood pressure at any point in time, $P_w$ at that time becomes more negative (moves further to the left on the horizontal axis).

With the definitions of the vertical axis V and the horizontal axis $P_w$ in mind, attention is now directed to an interpretation of the generally S-shaped cuff curve 12 within this coordinate system. For the moment, it is being assumed that this curve is characteristic of the particular patient being evaluated. That is, it is being assumed that the patient's artery within the cuff and therefore the cuff itself will change in volume along the S-shaped curve and only along the curve with changes in $P_w$. Hereinafter, with regard to FIG. 3, it will be shown that the arterial curve 12 of a given patient can be generated from his cuff pulses 10 and corresponding cuff pressures $P_c$. Thus, for the time being, it will be assumed that the arterial curve illustrated in FIG. 2 corresponds to that of the given patient.

With the foregoing in mind, the arterial curve of FIG. 2 will now be examined. Let it first be assumed that no pressure is applied to the patient's cuff so that $P_c$ equals zero. As a result, $P_w$ equals the blood pressure $P_b$ of the patient. In this regard, it is important to note that $P_b$ varies with time between the patient's diastolic blood pressure $P_b(D)$ and his systolic blood pressure $P_b(S)$. For purposes of this discussion, let it be assumed that these values are known and that specifically the patient's diastolic blood pressure is 80 Torr and his systolic blood pressure is 120 Torr. Thus, with no pressure in the cuff, $P_w$ oscillates back and forth with time between $P_b(D)$ and $P_b(S)$, that is, between 80 Torr and 120 Torr. This 40 Torr measuring band is illustrated by dotted lines in FIG. 2 at 14 and actually represents the patient's pulse pressure ΔP which is equal to 40 Torr in this case.

The patient's actual blood pressure waveform 15 is superimposed on the V/$P_w$ coordinate system in FIG. 2 within the pulse pressure band 14. As seen there, this waveform is made up of a series of actual blood pressure pulses 16, each of which corresponds to a single beat of the patient's heart. Note that each pulse starts at a minimum pressure (the diastolic pressure of the patient) and sharply increases along its leading edge which is the systolic rise $S_r$ until it reaches a maximum (the patient's systolic blood pressure), at which time it drops back down along a trailing edge which includes a dichrotic notch and a diastolic decline $D_d$ to the minimum pressure again.

At those points in time when the patient's blood pressure is at a minimum (that is, at the diastolic ends of pulses 16), the volume of the patient's artery and therefore the volume of the cuff is fixed by the arterial curve at the value indicated at $V_1(P_w=80)$. On the other hand, whenever the patient's blood pressure is maximum (at the systolic end of each blood pressure pulse 16), the arterial curve fixes arterial and therefore cuff volume at the slightly higher value indicated at $V_2(P_w=120)$. Therefore, it should be apparent that for each heart beat, assuming a cuff pressure $P_c$ of zero, the volume V (the cuff volume moves between the values $V_1$ and $V_2$, thereby generating a series of cuff pulses 10q corresponding to those illustrated in FIG. 1 but at a cuff pressure $P_c=0$, as shown in FIG. 1A. Thus, as the patient's blood pressure rises from a minimum to a maximum, the volume of the artery rises from $V_1$ to $V_2$ in a generally corresponding manner and as the patient's blood pressure drops back down to a minimum, the arterial volume falls from $V_2$ to $V_1$ in a generally corresponding manner. Thus, each of the arterial pulses 10 in FIG. 2 has a systolic rise $S_r$ and a diastolic decline $D_d$ corresponding to the systolic rise and diastolic decline of each blood pressure pulse 16.

Having shown how the cuff pulses 10q are dependent upon the volume curve at a cuff pressure of zero, we will now describe how the arterial curve causes these arterial pulses to change with applied cuff pressure. Let us assume now a cuff pressure of 50 Torr. Under these conditions, $P_w$ oscillates back and forth between 30 Torr and 70 Torr. The 30 Torr value is determined by subtracting the cuff pressure $P_c$ of 50 Torr from the diastolic blood pressure $P_b(D)$ of 80 Torr and the 70 Torr value is determined by subtracting the same $P_c$ of 50 Torr from the systolic blood pressure $P_b(S)$ of 120 Torr. Thus, the entire 40 Torr band has merely been shifted to the left an amount equal to 50 Torr as indicated by the band 14'. Under these circumstances, $P_w$ oscillates back and forth along a steeper segment of the arterial curve so as to cause the volume of the patient's artery and therefore the volume of the cuff to oscillate between the values $V_3$ and $V_4$. This results in the production of arterial pulses 101 at a $P_c$ of 50 Torr. Note that the amplitude of each cuff pulse 101 is greater than the amplitude of each cuff pulse 10q. This is because the 40 Torr band 14' at a cuff pressure of 50 Torr is on a steeper part of the volume slope than the band 14 at a cuff pressure of zero. Indeed, as we increase the cuff pressure $P_c$ (which decreases $P_w$) and therefore move the pressure band to the left on the horizontal axis, we first continue to move along steeper sections of the arterial curve and thereafter less steep sections. Therefore, the amplitude A (see FIGS. 1 and 1A) of the corresponding cuff pulses 10q, 101 and so on will first increase to a maximum and then decrease again. At a cuff pressure $P_c$ of 100, the entire 40 Torr pressure band is shifted to the left so as to uniformly straddle opposite sides of the vertical axis, as indicated at 14". This results in a corresponding cuff pulse 10g having approximately a maximum amplitude (ΔVmax in FIG. 2).

Moving still further to the left, at for example, a cuff pressure $P_c$ of 160 Torr, the entire 40 Torr band is moved a substantial distance to the left of the vertical axis, as indicated at 14''' such that the resultant change in volume (amplitude of the corresponding cuff pulse 10a) is quite small. By increasing the cuff pressure to even a greater amount, the band is moved still further to the left, eventually producing very small changes in volume V. From a physical standpoint, this represents a collapsed artery. In other words, sufficient cuff pressure $P_c$ is being applied over and above the internal blood pressure $P_b$ to cause the wall of the artery to collapse. At the other extreme, that is, when the cuff pressure $P_c$ is zero, there are no external constraints placed on the artery and the latter is free to fluctuate back and forth based on its internal pressure $P_b$ only. Between these extremes, the amplitude A of cuff pulse 10 (e.g. ΔV) will increase to a maximum and then decrease again, as stated. It is this characteristic of the volume curve which is used to determine the patient's systolic pressure in accordance with the previously recited Link et al patents, as will be described with regard to FIGS. 3 and 4.

As previously mentioned, it should be noted that a blood pressure increase causes an arterial volume increase. This arterial volume increase causes a cuff bladder air volume decrease which in turn causes a cuff bladder air-pressure increase. Therefore a blood pressure increase results in a cuff air pressure increase. This is emphasized as follows:

| blood pressure increase | → | arterial volume increase | → | cuff air volume decrease | → | cuff air pressure increase |
|---|---|---|---|---|---|---|
| Thus: | | blood pressure increase | → | cuff air pressure increase | | |

Referring to FIG. 3, the same arterial curve 12 illustrated in FIG. 2 is again shown but with a single superimposed pressure band 14'''' at a cuff pressure $P_c$ of 120 Torr. Assume again that the diastolic pressure of the patient is 80 Torr and his systolic pressure is 120 which means that $P_c$ is equal to the patient's systolic pressure. Under these circumstances, $P_w$ oscillates back and forth within band 14'''' between wall pressures of −40 Torr and zero, as shown. This results in a change in arterial volume ΔV (e.g., the amplitude A of a corresponding cuff pulse) which is approximately equal to one-half of the maximum change in arterial volume (e.g., max cuff pulse amplitude). It may be recalled that a maximum change in volume ΔV max (and therefore a maximum cuff pulse amplitude Amax) results from a cuff pressure $P_c$ of about 100 Torr (e.g. the pressure band 14" in FIG. 2). Thus, when the cuff pressure $P_c$ is equal to the patient's systolic blood pressure $P_b(S)$, the amplitude A of the resultant cuff pulse 10 is having a maximum amplitude. Therefore, a patient's systolic blood pressure can be determined by first generating a series of cuff pulses across the cuff pressure spectrum, as in FIG. 1A. From these pulses, the one having maximum amplitude Amax is determined and then the cuff pulse having half that amplitude (at a greater cuff pressure) is found. The cuff pressure $P_c$ used to generate that pulse corresponds to the patient's systolic pressure. In other words, by evaluating the amplitudes of the various cuff pulses, the one corresponding to the band $14''''$ illustrated in FIG. 3 can be found. Once that pulse is found, its associated cuff pressure is assumed to be equal to the patient's systolic pressure. This is discussed in more detail in Link et al U.S. Pat. Nos. 4,009,709 and 4,074,711 and means are provided in these latter patents for electronically making these evaluations.

Returning to FIG. 2, it should be noted that the actual blood pressure waveform 15 is shown having a uniform repetition rate, for example 60 pulses/minute, and that each blood pressure pulse 16 making up this waveform is identical to the next one. Both of these aspects of the waveform are assumed for purposes herein. Moreover, each pulse has its own systolic rise $S_r$ and diastolic decline $D_d$, as mentioned heretofore. It should also be noted that the arterial curve 12 dictates the relationship between V and $P_w$ at each and every point on the waveform 15 of individual blood pressure pulse 16, not merely at the extreme diastolic and systolic end points of each pulse. Thus, one could measure the change in volume $\Delta V$ at two different cuff pressures along the diastolic decline only. In this case, the measuring band (e.g. the pressure difference between the two measuring points) is substantially narrower than band 14. As best illustrated in FIG. 4, $\Delta V_1'$ is determined for a cuff pressure $P_c$ of zero using the pressure band 18 which encompasses a small part of the diastolic decline of each blood pressure pulse 16. $\Delta V_2'$ is determined for a cuff pressure of $P_c$ of 50 Torr by shifting the band to 18' and, $\Delta V_3'$ is determined for a cuff pressure $P_c$ of 80 Torr (e.g. the patient's diastolic blood pressure) by shifting the band to 18''. Note that $\Delta V$ is maximum when the cuff pressure $P_c$ is equal to the patient's diastolic blood pressure. Therefore, by determining the change in volume $\Delta V$ at the end of the diastolic slope of the patient's actual blood pressure waveform for each and every cuff pressure, the one cuff pressure producing a maximum change will correspond to the patient's diastolic blood pressure. The lowest pressure part of the diastolic decline $D_d$ forming part of each pulse 16 is particularly suitable for this purpose since it can be readily located during each cycle of the waveform. This is because it immediately precedes the systolic rise $S_r$ which is readily distinguishable each time it appears. This procedure is described in more detail in the previously recited Link U.S. Pat. No. 3,903,872 along with means for carrying out this procedure electronically.

The foregoing discussions for obtaining a given patient's systolic and diastolic blood pressures have assumed that the patient's arterial curve corresponded to the one illustrated in FIGS. 2, 3 and 4. While this assumption is reasonably valid, it is possible to determine the patient's own volume curve using the using the narrower bands 18, 18' and so on as measuring bands, the change in volume $\Delta V$ (e.g., the change in cuff volume) resulting from different cuff pressures $P_c$ is plotted, as shown in FIG. 5. Thus at a cuff pressure $P_c$ of zero, there is a relatively small change in volume $\Delta V$, as evidenced by the small $\Delta V_1'$ in FIG. 4. As the cuff pressure $P_c$ increases, the change in volume $\Delta V$ continues to increase to a maximum ($\Delta B_3'$ in FIG. 4) and then decreases. In mathematical terms, this curve represents incremental changes in volume with incremental changes in pressure or $dV/dP$ (FIG. 5). By integrating this curve we obtain the cuff curve or the V/P curve of FIGS. 2-4.

DETAILED DESCRIPTION

Having discussed FIGS. 1–5 in regards to the prior art techniques for obtaining diastolic and systolic blood pressures for a given patient in accordance with the techniques described in the above-recited Link and Link et al patents, attention is now directed to the various aspects of the present invention, as discussed briefly above, in conjunction with FIGS. 6–11 recited above.

Turning to FIGS. 6–9, a technique is provided for generating a waveform which closely approximates the actual blood pressure waveform of a patient. In order to more fully appreciate this technique, reference is again made to FIG. 2. It may be recalled that a particular patient's cuff pulses at any given cuff pressure is dictated by the S-shaped cuff curve 12 in FIG. 2. For example, assuming a systolic pressure of 120 Torr and a diastolic pressure of 80 Torr, the resultant measuring (pulse pressure) band may be moved along any section of the S-shaped curve by selecting a particular cuff pressure. Thus, with a cuff pressure of zero, the band is located to the far right, as viewed in FIG. 2 and by providing a cuff pressure of 160, the band is located to the far left. It is known that the most linear sections of the arterial curve provide cuff pulses which most approximate the actual blood pressure waveforms. To illustrate arbitrarily this known art the S-shaped cuff curve of FIG. 2 is shown in FIG. 6 divided into three sections, sections 2 and 3 being the least linear while section 1, is the most linear. Thus, if the pulse pressure band of FIG. 6 has its center along section 2 for example, that is, at a fixed cuff pressure of around 50 Torr, the resultant cuff pulses are not close approximations of the patient's actual blood pressure waveform. By operating in section 3, there is practically no gain at the diastolic end of the waveform, that is, this section of the curve is practically horizontal, resulting in very bad waveform distortions.

The most ideal section of the curve to operate on in order to produce fixed cuff pulses which most approximate the actual waveform is section 1 which is more linear and which displays moderate to low gain, that is, a gradual slope. This can be achieved by operating at a fixed cuff pressure of anywhere from zero to approximately 80 Torr. Once the cuff pressure is selected, corresponding cuff pulses of the given patient are continuously produced at the selected pressure. These cuff pulses are shown at $10m'$ in FIG. 7 and correspond to a cuff pressure of, for example, 40 Torr (see FIG. 1A). At the same time, the patient's systolic and diastolic pressures and arterial curve are used in combination with the cuff pulses to provide ultimately an approximation of the patient's blood pressure waveform, as will be seen below. The patient's arterial curve is reproduced in FIG. 7 at 12'. Both the systolic and diastolic pressures of the patient and curve 12' can be readily provided.

With the continuous pulses $10m'$ and curve 12' shown in FIG. 7, a waveform 16' can be generated between fixed wall pressures ($P_w$) which are dictated by the patients systolic and diastolic pressures and the cuff pressure selected. In the example above where the cuff pressure $P_c$ is 40 Torr, the patients systolic pressure $P_s$ is 125 and his diastolic pressure $P_d$ is 85, the operating $P_w$ band B is between 45 Torr and 85 torr, as illustrated in FIG. 7. These wall pressures dictate the section of curve 12' which produces waveform 16'. To generate this waveform from continuous pulses 10m', a first point $P_1$ at the beginning of pulse 10m' (at time $t_1$) is found and a corresponding point $P_1$ in band B is plotted. This is easily done since both of these points represent the diastolic pressure of the patient and the beginning of the pulse and waveform. A second point $P_2$ at time $t_2$ (as referenced from time $t_1$) can be found and so on until a series of points are found, as shown. From these points, the waveform 16 can be generated. The shape of waveform 16' correctly represents the true blood pressure waveform whereas the shape of waveform 10m' from which 16' is derived may be highly deformed by the arterial V/P curve.

In accordance with the present invention, suitable cuff means generally indicated at 30 in FIG. 8 is positioned around the arm of a patient in the normal operating manner and maintained at one of these preferably low pressures, for example, a cuff pressure of 40 Torr by pump means 32. However, the present invention is not limited to this cuff pressure range. Thus, for example, a cuff pressure of 100 Torr could be selected but higher cuff pressures of this type might be uncomfortable for the patient. The resultant cuff pulses are continuously monitored by transducer 34. Suitable and readily providable electronic circuitry 36 is also provided with the patients arterial curve and his systolic and diastolic pressures and uses the information to generate the waveform 16'. This waveform can be placed on an oscilloscope or monitor 38 or read out permanently as an approximation of the patient's actual blood pressure waveform, as shown in FIG. 1A. Moreover, in its displayed or readout state, the waveform can be appropriately labeled with its systolic and diastolic points in order to more aptly represent the patient's true blood pressure waveform.

In yet another application of the present invention, any single one or many of the cuff pulses obtained when the cuff pressure is ramped slowly down or up in pressure can be transformed by the apparatus described above into a waveform 16' which accurately represents the shape of the true blood pressure waveform. Thus during a normal oscillometric measurement of blood pressure as described elsewhere above, a single or many cuff pulses can be transformed into accurate representations of the blood pressure waveform and suitably presented on a monitor for a doctors examination.

The foregoing has been a discussion of how a particular patient's actual blood pressure waveform can be closely approximated without an invasive device. This may be an important diagnostic tool to a doctor, especially if it turns out that his patient has an unusual waveform. This is best exemplified in FIGS. 9a-d which diagrammatically illustrate a number of waveforms having different mean values. The mean pressure $P_b(m)$ of a blood pressure waveform is equal to the diastolic blood pressure $P_b(D)$ plus a particular fraction K of the pulse pressure which is the difference between the patient's systolic blood pressure $P_b(s)$ and his diastolic blood pressure. Equation 2A shows this and equation 2B shows the same thing in a convenient short hand notation and equation 2C solves equation 2B for K.

$$P_b(m) = P_b(D) + K(P_b(s) - P_b(D)) \quad (2A)$$

$$M = D + K(S - D) \quad (2B)$$

$$K = M - D/S - D. \quad (2C)$$

Noting that the mean pressure M can be calculated by integrating the waveform (its pressure amplitude P) over time T (the duration of the waveform) so that:

$$M = \frac{\int_0^T P \, dt}{T} \quad (3)$$

and:

$$K = \frac{M - D}{S - D} = \frac{\frac{\int_0^T P \, dt}{T} - D}{S - D} \quad (4)$$

With the above equations in mind, the FIG. 9a waveform can be shown to have a K value (which is commonly referred to as the blood pressure constant) of about 0.50. The FIG. 9b waveform approximates a K value of 0.6 while the FIG. 9c waveform approximates a K value of 0.2. Finally, the FIG. 9d waveform approximates a K value of 0.33. This latter waveform most closely corresponds to a healthy blood pressure waveform and therefore some diagnostic devices of the prior art purport to calculate mean blood pressures by assuming a K value of 0.33. With this assumption of K=0.33 along with the patient's diastolic and systolic blood pressures, a FIG. 9d waveform can be very approximately generated. Of course, this can be quite dangerous if the particular patient actually has a blood pressure constant of, for example, 0.60 or 0.20. However, in accordance with another aspect of the present invention, by generating the approximated waveform illustrated in FIG. 7, all guess work regarding the patient's blood pressure constant and mean blood pressure is eliminated. In fact, once the approximated waveform is determined, it can be integrated electronically so as to calculate the mean blood pressure $P_b(M)$ which might be helpful to the doctor and from this the blood pressure constant K can be readily calculated. Suitable means can readily be provided to make these various calculations.

As a result of the various aspects of the present invention described, a diagnostic tool can be provided which not only provides for a patient's diastolic and systolic blood pressures non-invasively but also a close approximation of the patient's actual blood pressure waveform as well as his mean pressure and blood pressure constant, again non-invasively. The means 30 shown in FIG. 8 can be provided with circuitry for calculating the mean pressure $P_b(M)$ and blood pressure constant K from this waveform and equations 2-4 above.

Having described the arrangement illustrated in FIG. 8, attention is now directed to FIG. 10 which illustrates the arrangement by means of a more detailed block diagram. As illustrated there, the arrangement includes the previously recited blood pressure cuff or cuff means 30. Means 32 in the form of a pump and suitable pneumatic controls are also illustrated and serve to pressurize the cuff to the previously recited different pressure levels. Pressure transducer 34 is shown coupling the cuff to a combination of amplifiers and band pass filters 40 for producing cuff pulses at different cuff pressures. An analog MUX and A/D converter and a sixteen-bit microcomputer or any other suitable computer means indicated generally at 42, 44 and 46, respectively, and connected in the manner illustrated in FIG. 10 cooperate to provide means for digitizing the analog cuff pressures, i.e., the cuff pressures Pc(dc) and the cuff pulses Pc(ac). The microcomputer or computer generally is controlled by a suitable program stored in ROM 48 in order to carry out the necessary steps of overall arrangement. This program may vary in length from for example 1K bytes to as much as 32K bytes depending upon accuracy and other factors. The digitized value of cuff pulses Pc(ac) and cuff pressures Pc(dc) are stored by computer 46 in a RAM 50. The computer can then act on information so stored to provide waveform 16' from cuff pulse 10m' in the manner described above. The computer can also integrate this waveform in the manner described above to provide mean pressure M and blood pressure constant K. These values can be readily read out, visually by for example monitor 52, or permanently, by means of, for example, printer 54 or by means of an LED display 56 or possibly another computer 58.

Turning now to FIG. 11, there is shown a flow diagram corresponding to the procedure described previously with respect to FIGS. 1–10 and incorporating the various steps carried out by the computer forming part of the block diagram illustrated in FIG. 10. Before proceeding with a description of this flow diagram, it should be noted that the term "Pc" therein refers to the combination of cuff pressure Pc(dc) and cuff pulses Pc(ac) and that the $\dot{P}c$ refers to the derivative of Pc and therefor the sum of the derivative of the cuff pressure $\dot{P}c$(dc) plus the derivative of the cuff pulses $\dot{P}c$(ac). It should be further noted that the derivative of the cuff pulses $\dot{P}c$(dc) corresponds to the ramp gradient characteristic resulting from the way in which the blood pressure cuff is pressurized. More specifically, as each cuff pulse Pc(ac) is generated at a given cuff pressure Pc(dc) it is done at continuously greater or lesser cuff pressures which form a continuously upwardly extending or downwardly extending ramp.

As will be seen below, the first ten steps (boxes) and box 14 in the flow diagram of FIG. 11 serve to receive physical cuff pressures from the cuff and these cuff pressures are converted to electrical analog signals and then digital signals and eventually the ramp component or gradient of the overall signal which is signal Pc is eliminated so as to provide the cuff pulses Pc(ac) by themselves on a horizontal axis rather than along a ramp gradient. At the same time, the overall signal Pc and the cuff pulses Pc(ac) are differentiated.

Referring now specifically to the flow diagram, step one begins after the start button is depressed and corresponds to pressurizing the cuff at different upwardly ramping or downwardly ramping cuff pressures Pc(dc). In step two the transducer forming part of the overall system receives the cuff pressures and converts them to analog signals which are filtered for 60 hz and noise (step three). These signals Pc are then differentiated by box four and the differentiated components $\dot{P}c$(ac) and $\dot{P}c$(dc) are alternately fed to an analog/digital converter (box six) by means of the multiplexor corresponding to box five. Both Pc and $\dot{P}c$ are stored in RAM as represented by box seven. As this is done, the system as represented by box eight continuously searches for the beginning of the cuff pulse by specifically looking for the beginning of its systolic rise. When that is found, $\dot{P}c$ is averaged (integrated) over a full pulse and therefore corresponds to $\dot{P}c$(dc) or the ramp gradient. Finally, as indicated in box ten, $\dot{P}c$(dc) is subtracted from $\dot{P}c$ leaving $\dot{P}c$(ac) which is the differential without the ramp gradient. Box fourteen integrates $\dot{P}c$(ac) to provide the cuff pulses by themselves, that is, without the ramp gradient. These separated cuff pulses and both Pc and $\dot{P}c$ are stored in RAM.

Steps one-ten and fourteen described previously provide the various cuff pulses Pc(ac). The flow diagram goes on to determine the subjects diastolic and systolic pressures and generates his transformation curve. Thereafter, as indicated by the flow diagram, a particular cuff pulse is selected and located on the transformation curve and thereafter transformed through the curve to obtain the second order approximation of the blood pressure pulse. This second order approximation waveform is displayed along with appropriate diastolic and systolic labels, as indicated by the flow diagram.

What is claimed is:

1. A non-invasive method of providing a waveform approximating the actual blood pressure pulse in a particular artery of a given mammal over a specific period of time during which a number of such pulses successively occur, each having diastolic and systolic pressure points, one edge defining a systolic rise and a second edge including a diastolic decline, said method comprising the steps of:
   (a) determining the diastolic and systolic blood pressures and the arterial curve of said mammal;
   (b) placing a blood pressure cuff around said particular artery;
   (c) pressurizing the cuff to a fixed pressure of a predetermined value and generating at least one or a series of cuff pulses at said fixed cuff pressure of a predetermined value from the blood pressure pulses in said artery; and
   (d) using said at least one or a series of cuff pulses, and the mammal's diastolic and systolic blood pressures and its arterial curve to generate a waveform which approximates the mammal's actual blood pressure waveform.

2. A method according to claim 1 wherein said cuff is ramped up and/or down in pressure to generate different cuff pulses at different cuff pressure values and wherein said waveform is responsive to each of said different cuff pulses.

3. A method according to claim 1 including the step of displaying said cuff pulse or pulses along with indicia indicating that the peak to peak amplitude of these pulses extends between specific pressure values corresponding to the mammal's diastolic and systolic pressures.

4. A method according to claim 3 wherein said cuff pulse or pulses are displayed on an oscilloscope.

5. A method according to claim 3 wherein only said cuff pulse or pulses, diastolic and systolic pressures and said arterial curve are used to generate said waveform.

6. A method according to claim 1 where said fixed cuff pressure is about zero and 60 Torr.

7. A method according to claim 6 wherein said cuff pressure is about 40 Torr.

8. A non-invasive apparatus providing a waveform approximating the actual blood pressure pulse in a particular artery of a given mammal over a specific period of time during which a number of such pulses successively occur, each having diastolic and systolic pressure points, one edge defining a systolic rise and a second edge including a diastolic decline, said apparatus comprising:

(a) means for determining the diastolic and systolic blood pressures and the arterial curve of said mammal;

(b) a blood pressure cuff for placement around said particular artery;

(c) means for pressurizing said cuff and cooperating with the pressurized cuff for generating at least one of a series of cuff pulses at a fixed cuff pressure of a predetermined value from the blood pressure pulses in said artery; and (d) means responsive to said at least one or a series of cuff pulses, and the mammal's diastolic and systolic blood pressures and its arterial curve for generating a waveform which approximates the mammal's actual blood pressure waveform.

9. An apparatus according to claim 8 including means for ramping up and/or down the pressure in said cuff to generate different cuff pulses at different cuff pressure values and wherein said waveform is responsive to each of said different cuff pulses.

10. An apparatus according to claim 8 including means for displaying said cuff pulse or pulses along with indicia indicating that the peak to peak amplitude of these pulses extends between specific pressure values corresponding to the mammal's diastolic and systolic pressures.

11. An apparatus according to claim 8 wherein said fixed cuff pressure is between zero and about 60 Torr.

12. A method according to claim 11 wherein said cuff pressure is about 40 Torr.

13. A non-invasive method of providing a waveform approximating the actual blood pressure pulse in a particular artery of a given mammal over a specific period of time during which a number of such pulses successively occur, said method comprising the steps of:

(a) determining the arterial curve of said mammal;

(b) placing a blood pressure cuff type member adjacent said particular artery;

(c) pressurizing the cuff-type member to a fixed cuff pressure of a predetermined value and generating at least one or a series of cuff pulses at said fixed cuff pressure of a predetermined value from the blood pressure pulses in said artery; and (d) using said at least one or a series of cuff pulses, and the mammal's arterial curve to generate a waveform which approximates the mammal's actual blood pressure waveform.

14. A method according to claim 13 wherein said fixed cuff pressure is between about zero and 60 torr.

15. A method according to claim 14 wherein said cuff pressure is about 40 torr.

16. A non-invasive apparatus providing a waveform approximating the actual blood pressure pulse in a particular artery of a given mammal over a specific period of time during which a number of such pulses successively occur, said apparatus comprising:

(a) means for determining the arterial curve of said mammal;

(b) a blood pressure cuff for placement adjacent said particular artery;

(c) means for pressurizing said cuff and cooperating with the pressurized cuff for generating at least one or a series of cuff pulses at a fixed cuff pressure of a predetermined value from the blood pressure pulses in said artery; and (d) means responsive to said at least one or a series of cuff pulses, and the mammal's arterial curve for generating a waveform which approximates the mammal's actual blood pressure waveform.

17. An apparatus according to claim 16 wherein said fixed cuff pressure is between about zero and 60 torr.

18. A method according to claim 17 wherein said cuff pressure is about 40 torr.

19. A non-invasive method of providing a waveform which is a second order approximation of the actual blood pressure pulse in a particular artery of a given mammal over a specific period of time during which a number of such actual blood pressure pulses successively occur, said method comprising the steps of:

(a) determining the arterial curve of said mammal;

(b) placing a blood pressure cuff type member adjacent said particular artery;

(c) pressurizing the cuff type member to a fixed cuff pressure of a predetermined value and form the blood pressure pulses in said artery generating at least one or a series of cuff pulses at said fixed cuff pressure of a predetermined value, said cuff pulses serving as a first order approximation of said actual blood pressure pulses, and (d) using said at least one or a series of cuff pulses, and the mammal's arterial curve to generate a waveform which is a second order approximation of the mammal's actual blood pressure waveform.

20. A non-invasive apparatus providing a waveform which is a second order approximation of the actual blood pressure pulse in a particular artery of a given mammal over a specific period of time during which a number of such actual blood pressure pulses successively occur, said apparatus comprising:

(a) means for determining the arterial curve of said mammal;

(b) a blood pressure cuff type member for placement adjacent said particular artery;

(c) means for pressurizing said cuff type member and cooperating with the pressurized cuff for generating at least one or a series of cuff pulses at a fixed cuff pressure of a predetermined value from the blood pressure pulses in said artery, said cuff pulses serving as a first order approximation of said actual blood pressure; and (d) means responsive to said at least one or a series of cuff pulses, and the mammal's arterial curve for generating a waveform which is a second order approximation of the mammal's actual blood pressure waveform.

* * * * *